United States Patent [19]
Sherman

[11] Patent Number: 5,968,552
[45] Date of Patent: Oct. 19, 1999

[54] DILTIAZEM HYDROCHLORIDE FORMULATION

[76] Inventor: Bernard Charles Sherman, 50 Old Colony Rd., Ontario, Canada, M2L 2K1

[21] Appl. No.: 08/849,324

[22] PCT Filed: Dec. 1, 1995

[86] PCT No.: PCT/CA95/00674

§ 371 Date: Jun. 2, 1997

§ 102(e) Date: Jun. 2, 1997

[87] PCT Pub. No.: WO96/17598

PCT Pub. Date: Jun. 13, 1996

[30] Foreign Application Priority Data

Dec. 6, 1994 [NZ] New Zealand ............... 270078

[51] Int. Cl.⁶ .................................................. A61K 9/64
[52] U.S. Cl. .................. 424/456; 424/490; 424/482; 424/489; 424/497
[58] Field of Search .................. 424/490, 452, 424/489, 468, 497, 484

[56] References Cited

U.S. PATENT DOCUMENTS

| | | | |
|---|---|---|---|
| 4,839,177 | 6/1989 | Colombo et al. | 424/482 |
| 5,286,497 | 2/1994 | Hendrickson et al. | 424/490 |
| 5,439,689 | 8/1995 | Hendrickson et al. | 424/490 |

FOREIGN PATENT DOCUMENTS

| | | |
|---|---|---|
| 0320097 | 6/1989 | European Pat. Off. . |
| 0386967 | 9/1990 | European Pat. Off. . |
| 3922167 | 1/1991 | Germany . |

*Primary Examiner*—Thurman K. Page
*Assistant Examiner*—William E. Benston, Jr.
*Attorney, Agent, or Firm*—Nixon & Vanderhye P.C.

[57] ABSTRACT

The invention relates to a pharmaceutical formulation comprising diltiazem hydrochloride. The formulation is in the form of a mixture of beads blended so as to provide a dissolution profile that renders the formulation suitable for oral administration once daily.

5 Claims, No Drawings

DILTIAZEM HYDROCHLORIDE FORMULATION

This application is a 371 of PCT/CA95/00674 filed Dec. 1, 1995.

FIELD OF INVENTION

A pharmaceutical formulation containing diltiazem hydrochloride suitable for once daily oral administration comprising a blend of beads having three differing dissolution profiles.

BACKGROUND OF THE INVENTION

Diltiazem is a benzothiazine derivative possessing calcium antagonist activity. Diltiazem blocks the influx of calcium ions in smooth and cardiac muscle and thus exerts potent cardio-vascular effects. Diltiazem has been shown to be useful in alleviating symptoms of chronic heart disease, particularly angina pectoris and myocardial ischemia and hypertension, while displaying a low incidence of side effects. The first dosage forms of diltiazem sold in the United States were tablets containing 30 mg or 60 mg of diltiazem hydrochloride sold under the tradename Cardizem by Marion Laboratories Inc. Single oral doses of 30 mg and to 120 mg of Cardizem tablets result in peak plasma levels about 2 to 3 hours after ingestion, and the elimination half-life is about 3 to 5 hours. Because of the relatively rapid absorption of diltiazem hydrochloride from such tablets and rapid elimination, the usual dosage regimen for immediate release tablets is for a dose to be taken three or four times daily. The need for such frequent administration may reduce patient compliance. Thus adverse therapeutic effects can arise. It thus became apparent that it would be preferable to administer diltiazem hydrochloride in a dosage form that releases the diltiazem hydrochloride much more slowly than Cardizem tablets, so as to enable the frequency of ingestion by the patient to be reduced to once daily.

A formulation of diltiazem hydrochloride that controls the rate of release to enable once daily administration is sold in the United States under the tradename Dilacor XR by Rhone-Poulenc Rorer Pharmaceuticals Inc.

Dilacor XR is produced as two-piece hard gelatin capsules, with each capsule containing a plurality of tablets. The 180 mg strength of Dilacor XR contains three tablets and the 240 mg strength contains four tablets. The same tablets are used in both capsules, and each tablet contains 60 mg of diltiazem hydrochloride.

The tablets used in Dilacor XR are made in accordance with the invention of U.S. Pat. No. 4,839,177.

Each tablet is comprised of a cylindrical core containing diltiazem hydrochloride mixed with inactive ingredients which include a polymer that swells and forms a gel upon contact with aqueous fluids. Because the gel has high viscosity it swells and dissolves only very slowly in the gastrointestinal fluids to thereby retard the rate of release of the diltiazem hydrochloride. To further retard the release, insoluble polymeric platforms are affixed to the top and bottom of the cylindrical core, thus leaving only the periphery exposed to the gastrointestinal fluid. The formulation of Dilacor XR capsules successfully accomplishes gradual release to enable once daily dosing, but the Dilacor XR formulation requires complex and expensive procedures to produce. In particular, production of the tablets contained in Dilacor XR capsules requires production of cores containing the diltiazem hydrochloride and the affixing thereto of the insoluble platforms.

Another formulation of diltiazem hydrochloride suitable for once daily administration is now sold in the United States under the trademark Cardizem CD, by Marion Laboratories Inc. Cardizem CD is sold as capsules containing a multitude of beads. The composition of the beads contained in Cardizem CD capsules is described in U.S. Pat. No. 5,286,497. The beads are made using core seeds to which is applied a first coating containing the diltiazem hydrochloride. Over the first coating, further coatings of polymers are applied which serve to slow down and control the rate at which the diltiazem hydrochloride is released from the beads in gastrointestinal fluids.

As explained in U.S. Pat. No. 5,286,497, there is a particular dissolution profile found to be optimum for once daily administration. This desired dissolution profile, when measured in a type 2 dissolution apparatus according to U.S. Pharmacopoeia XXII, in 0.1 NHCL at 100 rpm is as follows:

a) from 20–45% released after 6 hours
b) from 25–50% released after 12 hours
c) from 35–70% released after 18 hours
d) not less than 70% released after 24 hours
e) not less than 85% released after 30 hours The invention of U.S. Pat. No. 5,286,497 achieves this dissolution profile by using a mixture of beads with two differing amounts of coating.

The beads with the lesser amount of coatings are referred to as "rapid release diltiazem beads" and the beads with the greater amount of coating are referred to as "delayed release diltiazem beads".

It is disclosed that by making each of these types of beads so as to comply with particular dissolution requirements, the mixture of the two types of beads produces the desired dissolution profile for the final composition.

A difficulty with the invention of U.S. Pat. No. 5,286,497 is that it is difficult to reliably make the two types of beads so as to get the required dissolution profile for the final mixture.

In particular, the desired dissolution profile requires that the amount released must exceed 20% after 6 hours, but must not exceed 50% after 12 hours.

This requires that the "rapid release diltiazem beads" give a sharp step-like release of the diltiazem. Otherwise, if the amount released increases only gradually with time, beads formulated to assure that at least 20% of the diltiazem is released from the final mix after 5 hours will also cause more than 50% to be released after 10 hours, thus causing the final composition to fail to meet requirements.

In view of the aforesaid problems with prior art formulations, it is an object of the invention to produce a composition of diltiazem hydrochloride suitable for once daily administration, in the form of a blend of beads that overcomes the difficulty in achieving the required dissolution profile that results from using a mixture of only two types of beads.

OUTLINE OF THE INVENTION

The new formulation is characterized in the following way. Beads containing diltiazem hydrochloride are made by processes the same as or similar to those disclosed in U.S. Pat. No. 5,286,497.

However, instead of mixing only two types of beads, referred to as "rapid release beads" and "delayed release bead", three types of beads are made which will be referred to herein as "rapid release beads", "intermediate release beads", and "delayed release beads".

By using an appropriate mixture of these three types of beads, with three different amounts of coating, it is possible to obtain the desired dissolution profile for the final mix, without the need for the individual types of beads to have the sharp step-like release profile required by the invention of U.S. Pat. No. 5,286,497.

DETAILED DESCRIPTION OF THE INVENTION

The rapid release, intermediate release, and delayed release beads of the invention will typically exhibit in vitro dissolution profiles as shown in Table 1 when measured in 0.1 NHCL using a type 2 apparatus at 100 rpm according to U.S. Pharmacopoeia XXII.

TABLE 1

| Hours | RAPID RELEASE BEADS | | INTERMEDIATE RELEASE BEADS | | DELAYED RELEASE BEADS | |
|---|---|---|---|---|---|---|
| | Typical | Acceptable | Typical | Acceptable | Typical | Acceptable |
| 3 | 70% | 40% to 100% | 5% | 0% to 15% | 3% | 0% to 10% |
| 6 | 95% | 80% to 100% | 17% | 0% to 30% | 12% | 0% to 20% |
| 12 | 100% | 90% to 100% | 55% | 35% to 75% | 25% | 0% to 35% |
| 18 | 100% | 90% to 100% | 85% | 65% to 95% | 45% | 30% to 60% |
| 24 | 100% | 95% to 100% | 95% | 75% to 100% | 68% | 50% to 90% |
| 30 | 100% | 95% to 100% | 100% | 80% to 100% | 90% | 70% to 100% |

All three types of beads will usually be made by taking the same cores containing diltiazem hydrochloride and applying different amounts of polymeric coating to slow down the release. The intermediate release beads will typically have more coating than the rapid release beads, and similarly the delayed released beads will typically have more coating than the intermediate release beads.

It follows that the intermediate release beads will contain a smaller percent diltiazem hydrochloride by weight than the prompt release beads, and similarly the delayed release beads will contain a smaller percent diltiazem hydrochloride by weight than the intermediate release beads.

The final blend of beads will typically contain about 15% by weight rapid release beads, about 20% by weight intermediate release beads and about 65% by weight delayed released beads.

In view of the differences in percent diltiazem hydrochloride content as aforesaid, it follows that in the final blend, about 18% of the diltiazem hydrochloride content will be in the rapid release beads, about 20% in the intermediate release beads, and about 62% in the delayed release beads.

By taking into account these percentages along with the typical dissolution data given in Table 1, it can be seen that in the final mix, the dissolution at 6 hours will be about 27%, and at 12 hours will be about 44%.

There is thus achieved a final mix which has dissolution over 20% at 6 hours and under 50% at 12 hours, in accordance with the objective of this invention.

Similarly, it can be seen that in final mix the dissolution will be under 70% at 18 hours, over 70% at 21 hours, and over 85% at 30 hours.

The final mix can thus be made to meet the dissolution specifications disclosed in U.S. Pat. No. 5,286,497 as being particularly desired to ensure uniform blood levels, these specifications being as follows:

a) from 20% to 40% after 6 hours
b) from 25% to 50% after 12 hours
c) from 35% to 70% after 18 hours
d) not less than 70% after 24 hours
e) not less than 85% after 30 hours As aforesaid, all three types of beads will usually be made by first making core beads containing the diltiazem hydrochloride and then applying a polymeric coating to slow down the dissolution rate.

The core beads may be made by any of a number of techniques well known to persons skilled in the art of pharmaceutical formulations.

In one technique, the core beads are made beginning with sugar spheres having a diameter ranging from about 12 to 45 mesh and more preferably from 35 to 45 mesh. The spheres are loaded into a fluidized bed coating apparatus. In that apparatus there is sprayed onto the spheres a solution containing diltiazem hydrochloride, a polymeric binder and optionally other excipients. As the solvent is evaporated, a film containing diltiazem hydrochloride is built up to result in the core beads containing diltiazem hydrochloride.

Another technique suitable to produce core beads containing diltiazem hydrochloride is the technique known in the art as extrusion-spheronization.

In the extrusion part of this process, a mixture of diltiazem hydrochloride, a binder, water and optionally other excipients is forced through a screen to product moist strands. The moist strands are then transferred to the spheronizer. In the spheronizor the strands are placed on a rotating disc where they are forced to roll outward by centrifugal force. In the process, the strands break into pieces with length approximately equal to diameter, and they also become rounded as they roll. They are then dried and thus become dry core beads containing diltiazem hydrochloride.

As aforesaid, the second part of the process of producing the final beads is to apply to the core beads one or more polymeric coatings to slow down the dissolution rate.

Such coating or coatings may be applied by loading the core beads into a fluidized bed coating apparatus and spraying onto the core beads a solution or suspension of suitable polymers, and other excipients in a solvent, and evaporating the solvent. The solvent preferably will be water, but organic solutions also may be used.

This polymeric coating or coatings may be made using any number of polymers known in the art to be useful as slow-release coatings. Such polymeric coating may be produced, for example, using polymerized acrylates or copolymers of acrylic acid and methacrylic acid or esters of either monomer (hereinafter called polymerized acrylates. These materials are available from several commercial sources.

Examples of such copolymers include poly (methyl methacrylate), poly (ethyl methacrylate), poly (butyl methacrylate), poly (isobutyl methacrylate), poly (isobutyl methacrylate), and poly (phenyl methacrylate). The amount of polymerized acrylate contained within the polymeric coating can vary. Typically, the polymeric coating will contain from 10 to 75 w/w % of polymerized acrylate and preferably about 55–65 w/w % based on the total weight of the polymeric coating, the balance being a plasticizer and other excipients.

Preferred polymerized acrylates are those which are water insoluble, slightly water permeable copolymers of acrylic acid lower alkyl ester and methacrylic acid lower alkyl ester in which some ester moieties are further substituted with a tri(alkyl)ammonium group. The tri(alkyl)ammonium group is typically present in the range of about 1:30 to 1:50 relative to the amount of neutral ester present. One such preferred copolymer is a copolymer of ethyl acrylate and methyl methacrylate which contains trimethylammoniumethyl methacrylate in a range of about 1:40 relative to neutral monomers. This copolymer is commercially available from Rohm Pharma Gmbh under the tradename Eudragit RS. The same copolymer is available in an easy to use aqueous dispersion sold under the tradename Eudragit RS30D.

The polymeric coating will preferably contain a quantity of a suitable plasticizer. Examples of such plasticizers are acetyl triethyl citrate, dibutyl phthalate, tributyl citrate, triethyl citrate, acetyl triethyl citrate, propylene glycol, triacetin, polyethylene glycol and diethyl phthalate. Preferred plasticizers are triethyl citrate, tributyl citrate, and acetyl tributyl citrate.

The amount of plasticizer will typically be 5 to 30 w/w % based on the total weight of polymeric coating.

In addition to containing polymerized acrylate and optionally a plasticizer, the polymeric coating may contain other conventional excipients including antifoaming agents such as simethicone, in the range of 0 to 2 w/w % based on the total weight of the polymeric coating. It may also contain an anti-adherent such as talc in the range of 0 to 70 w/w % and preferably 25 to 35 w/w % based on the total weight of polymeric coating.

A sufficient quantity of polymeric coating must be utilized to substantially envelope the core beads in order to give them the desired release (i.e. dissolution) profile. The exact quantity will depend on the composition and size of the core beads, the composition of the coating, and whether the coated beads are intended to be the rapid release, intermediate release or delayed release beads. A suitable amount for each of the three types of beads can readily be determined by trial and error by persons skilled in the art. That is to say, various amounts can be applied and the dissolution profiles can be determined for the various amounts and a suitable amount thereby selected to give the desired profile.

For ease of handling the beads after application of the coating to the core beads it is desirable that the dried coating not be tacky, so that the beads will not stick together. Coatings of Eudragit RS and other similar polymers may be found to be excessively tacky. To solve this problems, a further coating may be applied over the tacky coating using another polymer that is not so tacky.

There are many suitable non-tacky polymers well-known in the art, including for example cellulose derivatives such as hydroxypropyl methylcellulose, which are water-soluble polymers. Another suitable nontacking polymer for such overcoat is a copolymer of methacrylic acid and methacrylic acid methyl esters sold by Rohm Pharma Gmbh under the tradename Eudragit L. This polymer is insoluble in gastric fluid but soluble in neutral to weakly alkaline intestinal fluid. As with Eudragit RS, Eudragit L is available in an easy to use aqueous dispersion sold under the tradename Eudragit L30D.

If an overcoat is used, unless it is rapidly soluble it will further delay the dissolution of the beads, and accordingly the amount of both the primary coating and the overcoating must be selected to achieve the desired dissolution profile for each of the three types of beads.

In the case of the rapid release beads, a coating as aforesaid is desirable but not necessary. That is to say, the rapid release beads may take the form of the core beads without coating. Alternatively the rapid release beads may consist of core beads coated with only a thin coating of a polymer that need not significantly delay dissolution, since there is no upper limit on the dissolution rate of the rapid release beads within the scope of the present invention.

After completion of coating and drying of the beads, the three types of beads are blended together in the required proportions for incorporation into the final dosage form.

The proportions of the three types of beads by weight will preferably be about 15% for the rapid release beads, about 20% for the intermediate release beads, and about 65% for the delayed release beads. However, the percentages may differ from these preferred amounts depending on the exact dissolution profile for each of the three types of beads.

The blended diltiazem beads may be administered in a number of dosage forms known in the art. For example, they may be placed into a gelatin capsule. The blended beads may also be mixed with a binder such as microcrystalline cellulose and compressed into tablets.

The quantity of beads that are placed in each dosage unit will typically be such as to produce a dosage unit containing from 90 mg to 540 mg of diltiazem hydrochloride, and more preferably from 120 mg to 360 mg. Such a dosage unit is suitable for once daily oral ingestion for a variety of cardiovascular indications such as angina, hypertension, and arrhythmias.

As used in this application, any reference to dissolution profile should be construed as referring to the results of a dissolution test in which the amount of diltiazem hydrochloride released is measured as specified in the United States Pharmacopoeia XXII, using a type 2 apparatus at 100 rpm, a temperature of 37° C. and a test solution of 0.1 NHCl.

The following examples are presented to further illustrate the invention but should not be considered as limiting the invention.

EXAMPLE 1

A quantity of core beads were made by the extrusion and spheronization process containing 90% by weight diltiazem hydrochloride, on a dried basis, the balance being microcrystalline cellulose together with methylcellulose as a binder.

EXAMPLE 2

Rapid release beads were made by coating the core beads of example 1 with a polymeric coating using Eudragit RS30D along with plasticizer and talc. An overcoating was then applied using Eudragit L30D along with plasticizer and talc. The total amount of coating applied was such as to give finished beads with the content of diltiazem hydrochloride being 77.3% by weight.

Gelatin capsules were filled with these beads and the dissolution profile was measured and found to be as shown in table 2, the results shown being the approximate average for several capsules.

TABLE 2

| Time | 3 hrs. | 6 hrs. | 12 hrs. | 18 hrs. | 24 hrs. | 30 hrs. |
|---|---|---|---|---|---|---|
| Amount released | 73% | 95% | 100% | 100% | 100% | 100% |

EXAMPLE 3

Intermediate release beads were made by coating the core beads of example 2 with a polymeric coating using Eudragit RS30D along with plasticizer and talc. An overcoating was then applied using Eudragit L30D along with plasticizer and talc. The total amount of both coatings was such as to give finished beads with the content of diltiazem hydrochloride being 63.9% by weight.

Gelatin capsules were filled with these beads, and the dissolution profile was measured and found to be as shown in table 3, the results shown being the approximate average for several capsules.

TABLE 3

| Time | 3 hrs. | 6 hrs. | 12 hrs. | 18 hrs. | 24 hrs. | 30 hrs. |
|---|---|---|---|---|---|---|
| Amount Released | 3% | 16% | 54% | 85% | 95% | 99% |

EXAMPLE 4

Delayed release beads were made by coating the core beads of example 2 with a polymeric coating using Eudragit RS30D along with plasticizer and talc. An overcoating was then applied using Eudragit L30D along with plasticizer and talc. The amount of Eudragit RS30D used was less than that used in making the beads of example 3, and the amount of Eudragit L30D used was more than that used in making the beads of example 3. The total amount of both coatings was such as to give finished beads with the content of diltiazem hydrochloride being 63% by weight.

Gelatin capsules were filled with these beads, and the dissolution profile was measured and found to be as shown in table 3, the results shown being the approximate average for several capsules.

TABLE 4

| Time | 3 hrs. | 6 hrs. | 12 hrs. | 18 hrs. | 24 hrs. | 30 hrs. |
|---|---|---|---|---|---|---|
| Amount Released | 3% | 12% | 26% | 44% | 68% | 88% |

EXAMPLE 5

The beads of examples 2, 3, and 4 were mixed in the following proportion.

| | |
|---|---|
| Rapid release beads from example 2 - | 15% |
| Intermediate release beads from example 3 - | 20% |
| Delayed release beads from example 4 - | 65% |
| Total - | 100% |

In view of the diltiazem hydrochloride percentage content contained in each of the three types of beads as stated in examples 2, 3, and 4, it will be seen that the diltiazem hydrochloride percentage content in the above mix is:

$$15\% \times 77.3\% + 20\% \times 63.9\% + 65\% \times 63\% = 65.3\%$$

To achieve a dose of 300 mg of diltiazem hydrochloride thus requires 300 mg/65.3% =459 mg of the mix of beads.

Gelatin capsules were filled each with 459 mg of this mixture of beads. The dissolution profile was measured and found to be as shown in table 5, the results shown being the approximate average for several capsules.

TABLE 5

| Time | 3 hrs. | 6 hrs. | 12 hrs. | 18 hrs. | 24 hrs. | 30 hrs. |
|---|---|---|---|---|---|---|
| Amount Released | 15% | 25% | 42% | 61% | 79% | 91% |

What is claimed:

1. A diltiazem hydrochloride formulation suitable for once daily oral administration comprising a blend of beads, such that the following dissolution profiles are satisfied when measured in a type 2 dissolution apparatus according to U.S. Pharmacopoeia XXII at 37° C. at 100 rpm in 0.1 NHCl:

i) a first portion of said beads exhibit the following profile:
  a) not less than 40% released at 3 hours
  ii) a second portion of said beads exhibits the following profile:
  a) not more than 30% released at 6 hours
  b) not less than 35% released at 12 hours
  iii) a third portion of said beads exhibits the following profile:
  a) not more than 20% released at 6 hours
  b) not more than 35% released at 12 hours
  c) not less than 50% released at 24 hours
  iv) the blend exhibits the following profile:
  a) from 20% to 45% released after 6 hours
  b) from 25% to 50% released after 12 hours
  c) from 35% to 70% released after 18 hours
  d) not less than 70% released after 24 hours
  e) not less than 85% released after 30 hours.

2. A formulation as in claim 1 wherein said beads are comprised of cores containing diltiazem hydrochloride in association with pharmaceutically acceptable excipients and a polymeric coating which envelopes said cores.

3. A formulation as in claim 1 wherein said first portion of beads constitutes from 5% to 25% of the totality of beads by weight, said second portion of beads constitutes from 10% to 30% of the totality of beads by weight, and said third portion of beads constitutes from 50% to 75% of the totality of beads by weight.

4. A formulation as in claim 2 wherein the polymeric coating on some or all of the beads contains polymerized acrylate and a plasticizer.

5. The formulation of claim 1 contained within a gelatin capsule.

* * * * *